United States Patent

Stanzl et al.

[11] Patent Number: 5,885,558
[45] Date of Patent: Mar. 23, 1999

[54] SUN PROTECTION PREPARATION WITH AN INCREASED SUN PROTECTION FACTOR

[75] Inventors: Klaus Stanzl, White Plains, N.Y.; Leonhard Zastrow, Monaco, Monaco; Rupali Kulkarni, Bridgewater; Domnica Cernasov, Ringwood, both of N.J.

[73] Assignee: Lancaster Group GmbH, Ludwigshafen, Germany

[21] Appl. No.: 836,005

[22] PCT Filed: Nov. 23, 1995

[86] PCT No.: PCT/DE95/01701

§ 371 Date: May 6, 1997

§ 102(e) Date: May 6, 1997

[87] PCT Pub. No.: WO96/15772

PCT Pub. Date: May 30, 1996

[30] Foreign Application Priority Data

Nov. 24, 1994 [DE] Germany .................. 44 43 243.7

[51] Int. Cl.⁶ .................. A61K 7/42; A61K 7/44; A61K 7/00
[52] U.S. Cl. .................. 424/59; 424/60; 424/400; 424/401

[58] Field of Search .................. 424/59, 60, 400, 424/401

[56] References Cited

FOREIGN PATENT DOCUMENTS

| | | |
|---|---|---|
| 197485 | 10/1986 | European Pat. Off. . |
| 430473 | 6/1991 | European Pat. Off. . |
| 557089 | 2/1993 | European Pat. Off. . |
| 4221269 | 12/1993 | Germany . |
| WOA9311095 | 3/1993 | WIPO . |
| WOA9311742 | 6/1993 | WIPO . |
| WO 93/19729 | 10/1993 | WIPO . |
| Wo 94/06409 | 3/1994 | WIPO . |
| WOA9418940 | 9/1994 | WIPO . |

*Primary Examiner*—Shelley A. Dodson
*Attorney, Agent, or Firm*—Collard & Roe, P.C.

[57] ABSTRACT

The invention concerns a sun-protection preparation with an increased light-protection factor, consisting of (A) a fine-particle, crosslinked poly(methylsiloxane) with a particle size ranging from 1 to 10 $\mu$m, the poly(methylsiloxane) having given further parameters, (B) octyldodecylneopentanoate, (C) formulation aids, and (D) additives. The ratio of (A) to (B) ranges from 1:2 to 10, and the portion of (A) and (B) ranges from 3 to 12 wt %, relative to the total composition.

9 Claims, No Drawings

SUN PROTECTION PREPARATION WITH AN INCREASED SUN PROTECTION FACTOR

This invention relates to a sun protection preparation with an increased sun protection factor.

Numerous sun protection preparations have become known. Topical sun protection preparations, as a rule, can either be categorized as chemical or physical sun protection preparations. The chemical sun protection preparations that are of interest here contain one or several UV-absorbing substances and, after a thin and invisible film of such preparation has been applied to the skin, act as a screen preventing ultraviolet radiation from penetrating to the living cells of the epidermis. Chemical sun protection preparations are usually colourless as they do not contain any substances that absorb visible light, and they are therefore cosmetically acceptable for most people provided that they do not irritate the eyes, are non-photosensitizing, stable and non-volatile, and that they do not leave any stains on people's skin and clothing. Most commercial sun protection preparations contain one or several chemicals which absorb UV-B radiation, and furthermore they contain a moisturizing base. A more recent ingredient of known sun protection preparations have been UV-A radiation-absorbing substances, mostly various benzophenones. Most chemical sun protection preparations used comprise p-aminobenzoic acid (PABA), PABA esters (amyl dimethyl PABA and octyl dimethyl PABA), benzophenones, cinnamates (octyl methoxycinnamate and cinnoxate), salicylates (homomenthyl salicylate), and anthranilates.

Sun protection preparations that contain a-hydroxy acids or their derivatives have been known from WO 94/06409 (PCT/US92/11037) by Perricone et al. Furthermore, sun protection preparations have been known from WO93/19729 (PCT/US93/02712) that contain a combination of retinoic acid and various derivatives thereof with pharmaceuticals.

WO93/11742 (PCT/EP92/02897) proposes a portion of 0.5 to 30 wt % of titanium dioxide and/or zinc oxide, or 0.001 to 2 wt % of iron oxide, the mean primary particle size of said iron oxide being about 200 nm. These particles may also be coated with phospholipids.

It has become a generally accepted practice to specify the sun protection factor (SPF) of sun protection preparations. There is a great interest in increasing said sun protection factor so that the product can be used by many people and invariably causes a pleasant dermal sensation. The medium-range sun protection factors from SFP 10 to 20 are of particular interest in this respect.

It is therefore the object of the invention to provide novel sun protection preparations having an improved sun protection factor.

A sun protection preparation according to the invention consists of
(A) a fine-particle, crosslinked poly(methylsiloxane) with a particle size ranging from 1 to 10 μm;
(B) octyldodecyl neopentanoate;
(C) formulation aids; and
(D) additives.

The ratio of (A) to (B) ranges from 1:2 to 10, and the portion of (A) and (B) ranges from 3 to 12 wt %, relative to the total composition.

A particularly advantageous preparation contains the component (A) with a mean particle size of 4.5 μm.

In another preferred embodiment, the ratio of (A) to (B) ranges from 1:2.5 to 8, preferably from 1:3 to 5.

In yet another preferred embodiment, the total portion of components (A) and (B) is 4 to 8 wt %, relative to the total composition.

The fine-particle, crosslinked poly(methylsiloxane) which constitutes component (A) is a product that specifically has the following properties:
its weight loss is 3% or less at 350° C., and 12% or less at 900° C.;
the particle diameter does not change when calcined in air for four hours up to about 350° C. and is reduced by 25% or less at 900° C. While retaining its generally circular structure;
there are no endothermic peaks when heated in air at a heating rate of 10° C. per minute;
it is resistant to organic solvents based on alcohols, ketones, esters, aromates, and chlorinated hydrocarbons.

A particularly advantageous poly(methylsiloxane) is the commercial product named Tospearl®, in particular Tospearl 145® by Toshiba Silicone Co., Ltd., available from Kobo Products, Inc., N.J., U.S.A.

It is known that component (B), octyldodecyl neopentanoate (CTFA name), is an emollient. A particularly advantageous commercial product is Elefac I 205® (available from Bermel Chem. Comp., Englewood, N.J., U.S.A.). When this component (B) is used in a preparation with UV screens and other common adjuvants and additives, a sun protection factor of about 16 is obtained.

Surprisingly, the sun protection factor is increased up to about 18 or 19 when adding small quantities of poly (methylsiloxane) as component (A). Although it has been known that the crosslinked polymer (A) is highly heat-resistant, there was no information as to its influence on UV radiation.

The components (A) and (B) can be encapsulated in common liposomes.

In a particularly advantageous embodiment, components (A) and (B) are present in asymmetric lamellar aggregates consisting of phospholipids and fluorocarbons charged with oxygen or fluorocarbon mixtures, the portion of fluorocarbon ranging from 0.2 to 100% w/v, the phosphatidylcholine content of the lipid fraction being from 30 to 99 wt %, and comprising skin penetration capability depending on the critical solubility temperature of fluorocarbons (into n-hexane). The incorporation of the components (A) and (B) in said novel asymmetric lamellar aggregates known from WO94/00098 may facilitate the particularly deep penetration of the components that act against UV radiation, which may contribute to improving sun protection.

Unlike the known aqueous liposomes (vesicles), these hydrophobic phospholipid-stabilized aggregates carry hydrophobic fluorocarbons in their core that are capable of transporting oxygen. They are primarily stabilized at their interfacial surfaces by an inversely arranged monolayer and, optionally, subsequent formulation of bilayers. These novel aggregates are called asymmetric lamellar oxygen carriers because of their structural peculiarities. The extraordinary colloidochemical stability of these aggregates is probably due to their lamellar structure and to their surface charge. The latter is based on selecting suitable phospholipids or natural or synthetic mixtures thereof. The substances responsible for an advantageous effect are, first of all, phospholipids, especially phosphatidylcholine at the specified concentration of 30 to 99% combined with lysolecithins having a concentration of 0.1 to 10% and/or charged phospholipids with concentrations ranging from 0.1 to 30 wt %. The specified effect of the phospholipids is verified by the respective negative zeta potentials and by charge density measurements (during titration with a cationic polyelectrolyte). Penetration of the skin as a function of the critical solubility temperature of the fluorocarbons or fluorocarbon mixtures selected is essential for the use of fluorocarbon aggregates (for using asymmetric lamellar aggregates, see also DE-B-42 21 255).

The portion of aggregates charged with sun-protective components may range from 5 to 60 wt %, relative to the total preparation, preferably in the range from 10 to 50 wt %, most preferred from 30 to 50 wt %.

As has been said above, common liposomes can be used as a transport system for the modified clay-containing mixture contained in the preparation of the invention. Liposomes are totally enclosed lipid-bilayer membranes encompassing an aqueous volume. Liposomes can be unilamellar vesicles (comprising a single-membrane bilayer) or multilamellar vesicles (onionlike structures characterized by multiple-membrane bilayers, each of which being separated from the next by an aqueous layer). The bilayer consists of two lipid monolayers that have a hydrophobic tail section and a hydrophilic head section. The bilayers are structured in such a way that the hydrophobic (non-polar) tails of the lipid monolayers are oriented towards the centre of the bilayer whereas their hydrophilic heads are oriented towards the aqueous phase.

The production of liposomes from saturated or unsaturated lipids and their use as transport systems have been described in numerous patents. The modified clay-containing mixture can be worked in in a generally known way.

Other ingredients of the sun protection preparation of the invention are additional UV-B screens that may be oil- or water-soluble. These include, for example, derivatives of aminobenzoic acid, esters of cinnamic acid, esters of salicylic acid, benzophenone derivatives and sulfonic acid derivatives of benzophenone, sulfonic acid derivatives, sulfonic acid derivatives of 3-benzyledene camphor, etc. Furthermore, inorganic pigments such as oxides of titanium, zinc, iron, circonium, silicium, manganese, aluminium, or mixtures thereof may be used. When including inorganic pigments, however, it should be noted that their agglomeration has to be balanced by adding larger quantities of emulgators. In addition, so-called radical traps such as α-tocopherol or tocopheryl acetate may be used. As the products of photochemical reactions frequently are radicals, e.g. hydroxy radicals, hydroxyperoxy radicals, or superoxide ions and singlet oxygen, other radical traps that are suitable for cosmetic preparations may be used, e.g. transurocanic acid.

The preparation of the invention further contains other adjuvants that are common in similar preparations. This includes stabilizers such as PEG-8, BHT (Protegol®), crosslinked alkyl acrylates (Pemulen®) as well as preservatives such as phenoxy ethanol, parabens, methyl dibromoglutaronitrile, benzophenone-3, etc. and other gels and fragrances. Moreover, the preparation may contain plant extracts of aloe vera and others.

The sun protection preparation of the invention with an increased sun protection factor is produced using an emulsification method in which the ingredients are intermixed, optionally after separate emulsification at increased temperatures. It is advantageous in this respect to add the component (A) immediately after the oil phase in the emulsification process. After bringing about sufficient homogenization, the homogenate is cooled down to room temperature, and preservatives and fragrances are added. It goes without saying that all processing has to take place under sterile conditions.

If the sun protection preparation contains the asymmetric lamellar aggregates mentioned above, the components (A) and (B) are subsequently added to a perfluorocarbon while being properly homogenized and, optionally, mixed with glycerine and propylene glycol, and a phospholipid with a phosphatidylcholine content of more than 30% is added under stirring to this homogenate. Subsequently, water is added. After proper homogenizing, the aggregates charged with light-protective components are available for further intermingling with the suspension. If other light-protective components are to be contained in the finished preparation, these may also be intermingled with said aggregates.

A particularly advantageous embodiment of the sun protection preparation according to the invention may be an emulsion or spray. If the preparation of the invention is formulated as a spray, it may be added with the typical known substances contained in a spray such as propellants, especially non-polluting propellants, so that the product is ready for use in an aerosol spray can.

The invention shall now be explained in greater detail based on examples. The percentages given in these examples are percentages by weight.

EXAMPLE 1

| | |
|---|---|
| Phenyltrimethicone | 5.00% |
| Tocopheryl acetate | 2.00% |
| Octyldodecyl neopentanoate | 4.00% |
| Bisabolol | 0.50% |
| Isostearyl neopentanoate | 1.50% |
| BHT | 0.07% |
| Acrylate/C10–30 alkyl acrylate crosspolymer | 0.25% |
| Benzophenone-3 | 2.00% |
| Octyl methoxycinnamate | 7.50% |
| 2-Phenylbenzimidazole-5-sulfonic acid | 16.00% |
| Panthenol & propylene glycol | 3.00% |
| Acrylates copolymer & melanin & PPG-2 myristyl ether propionate & methylparaben & propylparaben | 0.20% |
| Aloe vera gel | 0.10% |
| Disodium EDTA | 0.05% |
| PEG-8 | 5.00% |
| Carbomer | 0.20% |
| Polymethylsilsesquioxane (Tospearl 145 ®) | 1.00% |
| Phenoxyethanol & (Methyl-ethyl-propyl-butyl) parabens | 0.50% |
| Methyldibromo glutaronitrile & phenoxyethanol | 0.50% |
| Fragrance | 0.50% |
| Water | ad 100 |

The preparation was produced as follows: an aqueous and an oil phase were emulsified by homogenization at the usual temperatures in the range from 50° to 75° C. The aqueous phase was added with disodium EDTA, PEG-8, aloe vera, then polymethylsilsesquioxane, and finally the carbomer. After the batch had turned into a dispersion and been heated to approx. 70° C., 2-phenylbenzimidazol-5-sulfonic acid was added.

The oil phase was produced by mixing phenyl trimethicone, tocopheryl acetate, octyldodecyl neopentanoate, bisabolol, isostearyl neopentanoate, and BHT, and by preheating this mixture to 60° C. octyl methoxycinnamate and benzophenone are simultaneously mixed and slightly heated, and added to the oil phase. Finally, acrylate/C10-30 alkyl acrylate crosspolymer is added while the mixture is properly homogenized until a dispersion of the oil phase is obtained.

After emulsifying the oil and the aqueous phases and cooling to about 40° C., acrylates copolymer & melanin & PPG-2 myristyl ether propionate & methylparaben & propylparaben and panthenol/propylene glycol is added followed by protective agents and fragrance components.

EXAMPLE 2

Liposomes

A phospholipid with soluble animal collagen and hydrolysed mucopolysaccharides was placed in an aqueous suspension of polymethylsilsesquioxane and octyldodecyl neopentanoate. After proper homogenization, this suspension was added to the dispersion obtained in Example 1 containing the other ingredients, then homogenizing was continued so that the portion of liposomes was approx. 5%.

EXAMPLE 3

Aggregates

A perfluorocarbon (perfluorodecaline) mixed with glycerin and propylene glycol was intermixed with polymethylsilsesquioxane and octyldodecyl neopentanoate, and a phospholipid containing 40% of phosphatidylcholine was added to this mixture. The mixture was properly homogenized. The asymmetric lamellar aggregates that were formed in this process were added to the dispersion containing the other ingredients of the formulation in accordance with Example 1 so that the total portion of liposomes was approx. 5%.

REFERENCE EXAMPLE 1

The processing was performed as in Example 1 except that the fine-particle, crosslinked poly(methylsiloxane) (CFTA name: polymethylsilsesquioxane) was not contained and that the portion of octyldodecyl neopentanoate was only 2.00%. Mixing was performed in a similar way as in Example 1. The sun protection factor obtained for the formulation was below 16.16 (prior to immersion) and below 15.84 after immersion.

The sun protection factor of the formulation prepared in accordance with Example 1 was 19.80 (prior to immersion) and 17.00 after immersion.

The sun protection factor was measured in accordance with a regulation issued by the U.S. Food and Drug Administration (FDA) by exposing a group of 5 people treated with the sun protection preparation of the invention and with the preparation of the reference example to the 150 W xenon arc lamp of a 10 S solar ultraviolet simulator.

The results show that the sun protection factor could be significantly increased by adding poly(methylsiloxane).

We claim:

1. A sun protection preparation comprising
   (A) a fine-particle, crosslinked poly(methylsiloxane) with a particle size ranging from 1 to 10 μm, and having the following parameters:
   said poly(methylsiloxane) having a weight loss of 3% or less at 350° C., and 12% or less at 900° C.;
   said particle having a diameter which does not change when calcined in air for four hours up to about 350° C. and is reduced by 25% or less at 900° C. while retaining its generally circular structure;
   there is no endothermic peak when heated in air at a heating rate of 10° C. per minute;
   said poly(methylsiloxane) being insoluble in organic solvents based on alcohols, ketones, esters, aromates, and chlorinated hydrocarbons;
   (B) octyldodecyl neopentanoate;
   (C) formulation aids; and
   (D) additives;
   wherein the ratio of (A) to (B) ranges from 1:2 to 10, and the portion of (A) and (B) ranges from 3 to 12 wt %, relative to the total composition.

2. The sun protection preparation according to claim 1 wherein the mean particle size is 4.5 μm.

3. The sun protection preparation according to claim 1 wherein the ratio of (A) to (B) ranges from 1:2.5 to 8.

4. The sun protection preparation according to claim 1 wherein the portion of (A) and (B) ranges from 4 to 8 wt %, relative to the total composition.

5. The sun protection preparation according to claim 1, further comprising liposomes encapsulating the fine-particle, crosslinked poly(methylsiloxane) and component (B).

6. The sun protection preparation according to claim 1 wherein (A) and (B) are present in the form of asymmetric lamellar aggregates consisting of phospholipids and fluorocarbons or fluorocarbon mixtures charged with oxygen, the portion of fluorocarbons ranging from 0.2 to 100% w/v, and the phosphatidylcholine content of the lipid fraction being 30 to 99 wt %, and wherein the penetration of the skin by said aggregates is dependent upon the critical solubility temperature of the fluorocarbons.

7. The sun protection preparation according to claim 1, wherein the formulation is present in the form of a lotion.

8. The sun protection preparation according to claim 1, wherein the ratio of (A) to (B) is 1:5.

9. The sun protection preparation according to claim 1, wherein the formulation is present in the form of a spray.

* * * * *